(12) United States Patent
Bachem et al.

(10) Patent No.: US 9,091,533 B2
(45) Date of Patent: Jul. 28, 2015

(54) OPTICAL SURVEILLANCE DEVICE

(75) Inventors: Alexander Bachem, Darmstadt (DE); Matthias Westenhoefer, Offenburg (DE); Karlheinz Hohm, Moemlingen (DE)

(73) Assignee: ISRA VISION AG, Darmstadt (DE)

( * ) Notice: Subject to any disclaimer, the term of this patent is extended or adjusted under 35 U.S.C. 154(b) by 1293 days.

(21) Appl. No.: 12/477,383

(22) Filed: Jun. 3, 2009

(65) Prior Publication Data

US 2010/0007733 A1 Jan. 14, 2010

(30) Foreign Application Priority Data

Jun. 6, 2008 (DE) .................... 20 2008 007 630 U
Jun. 9, 2008 (DE) .......................... 10 2008 027 393

(51) Int. Cl.
*H04N 7/18* (2006.01)
*G01N 21/00* (2006.01)
*G01B 11/24* (2006.01)
*G02B 5/08* (2006.01)
(Continued)

(52) U.S. Cl.
CPC ............. *G01B 11/24* (2013.01); *B05C 5/0216* (2013.01); *G01C 1/04* (2013.01); *G01C 15/00* (2013.01); *G01N 21/8901* (2013.01); *G01N 2021/845* (2013.01); *G01N 2201/068* (2013.01); *G02B 5/08* (2013.01); *G02B 7/003* (2013.01); *G02B 21/084* (2013.01); *G02B 23/2476* (2013.01); *H04N 5/2254* (2013.01); *H04N 21/4223* (2013.01)

(58) Field of Classification Search
CPC ............. H04N 5/2254; H04N 21/4223; G02B 21/084; G02B 23/2476; G02B 5/08; G02B 7/003; G01C 15/00; G01C 1/04; G01N 2021/845; G01N 2201/068; G01N 21/8901
USPC .......................................... 348/143; 356/240.1
See application file for complete search history.

(56) References Cited

U.S. PATENT DOCUMENTS 5,699,152 A * 12/1997 Fedor et al. ................. 356/240.1
5,912,776 A * 6/1999 Yaginuma ...................... 359/850

(Continued)

FOREIGN PATENT DOCUMENTS

DE 40 00 988 5/1991
DE 199 48 837 4/2001

(Continued)

OTHER PUBLICATIONS

Asada, H.; Rabou, N.A.; Ikeda, H.; Shimodaira, Y.; Yoshida, H., "Transmission rate reduction in monitoring two-dimensional moving images in factory automation," Industry Applications Conference, 1997. Thirty-Second IAS Annual Meeting, IAS '97., Conference Record of the 1997 IEEE , vol. 2, no., pp. 912,918 vol. 2, Oct. 5-9, 1997.*

(Continued)

*Primary Examiner* — Taylor Elfervig
(74) *Attorney, Agent, or Firm* — Michael J. Striker

(57) ABSTRACT

The invention proposes an optical monitoring device for monitoring the activity of a tool in a monitoring area, having at least one camera (1). In order to improve the capture of the lateral regions of a three-dimensional object in the monitoring area (20), at least one mirror (2) is provided that is concavely bent in at least one partial region and that is disposed in the optical path between the monitoring area (20) and the camera (1).

14 Claims, 1 Drawing Sheet

(51) Int. Cl.
  *G01C 15/00* (2006.01)
  *G02B 23/24* (2006.01)
  *G02B 21/08* (2006.01)
  *G01N 21/84* (2006.01)
  *G02B 7/00* (2006.01)
  *G01N 21/89* (2006.01)
  *H04N 21/4223* (2011.01)
  *H04N 5/225* (2006.01)
  *G01C 1/04* (2006.01)
  *B05C 5/02* (2006.01)

(56) References Cited

U.S. PATENT DOCUMENTS

| | | | |
|---|---|---|---|
| 6,775,012 B2 | 8/2004 | Wurz et al. | |
| 2003/0020916 A1 | 1/2003 | Ghilai et al. | |
| 2005/0099605 A1* | 5/2005 | Buchner | 353/31 |
| 2007/0236565 A1 | 10/2007 | Tropf | |
| 2007/0292629 A1 | 12/2007 | Linnenkohl et al. | |
| 2008/0024602 A1 | 1/2008 | Linnenkohl et al. | |
| 2008/0137088 A1* | 6/2008 | Wagner | 356/446 |
| 2010/0045988 A1* | 2/2010 | Hietanen et al. | 356/430 |

FOREIGN PATENT DOCUMENTS

| | | |
|---|---|---|
| DE | 203 07 305 | 7/2003 |
| DE | 10 2006 008 552 | 4/2007 |
| DE | 10 2006 006 204 | 8/2007 |
| DE | 10 2006 036 586 | 2/2008 |
| DE | 10 2007 031 835 | 1/2009 |
| EP | 1 697 061 | 9/2006 |
| EP | 1 701 801 | 9/2006 |

OTHER PUBLICATIONS

Shigang Li, "Monitoring Around a Vehicle by a Spherical Image Sensor," Intelligent Transportation Systems, IEEE Transactions on, vol. 7, No. 4, pp. 541,550, Dec. 2006.*

Kinoshita, H.; Hoshino, K.; Matsumoto, K.; Shimoyama, I., "Thin compound eye camera with a zooming function by reflective optics," Micro Electro Mechanical Systems, 2005. MEMS 2005. 18th IEEE International Conference on, vol., no., pp. 235,238, Jan. 30-Feb. 3, 2005.*

* cited by examiner

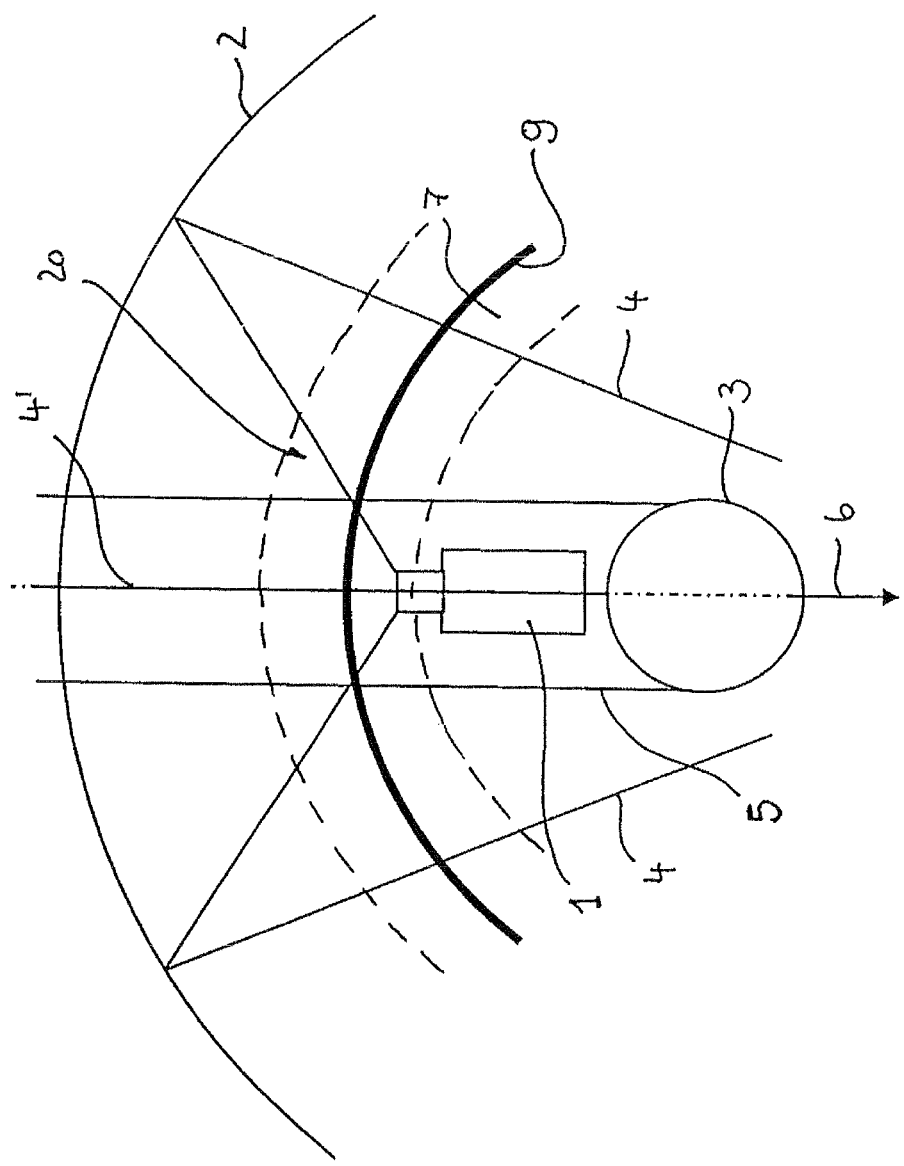

OPTICAL SURVEILLANCE DEVICE

BACKGROUND OF THE INVENTION

The present invention relates to an optical monitoring device for monitoring the activity of a tool in a monitoring region, having at least one camera.

Such a monitoring device is suitable for many types of tools and is not limited to any one particular type of tool; therefore, the tool may be, for example, a welding, riveting, or soldering device, a device for applying adhesive, for example, in the form of an adhesive bead, to a workpiece to be adhered, a common sensor element, for example, for scanning surfaces, or any sort of implement or application tool, the activity of which must be monitored. Other areas of application for such a monitoring device are inspection, for example, in the context of quality control and/or the processing of objects such as an adhesive bead, a seam, a joint, and edge, and/or a surface. An optical monitoring device according to the invention is particularly suitable for robotically operated tools whose function must be monitored.

The monitoring device monitors the activity of such a tool in a monitoring area that may include, for example, the immediate working area of the tool. The term "working area of the tool" is to be understood in this context as the three-dimensional area in which the tool operates. Moreover, the monitoring area may also comprise an optionally three-dimensional area that is not the working area of the tool but preferably is associated with the activity of the tool, for example, an area adjacent to the working area that is used for quality control of the object processed in the working area.

An optical monitoring device for monitoring a working area and/or monitoring area having at least one camera is disclosed in DE 203 07 305 U1. The known monitoring device may be fixed to the tool such that the visual range of the camera is always directed at the monitoring area, even if the tool and/or an object to be processed moves. In a preferred embodiment, the optical monitoring device is embodied such that the visual ranges of at least two, preferably three, cameras overlap in the monitoring area.

EP 1 697 061 B1 and EP 1 701 801 B1 disclose a similar device for detecting a structure to be placed on a substrate, preferably an adhesive bead or adhesive track. The sensor unit of such a device comprises a plurality of cameras, with the cameras each being directed towards the unit for applying the structure and being disposed around said unit.

However, the methods mentioned above have the disadvantage that the field of view of a camera cannot be used sufficiently in measuring a three-dimensional object (for example, an adhesive bead), particularly with regard to analyzing the sides of the object. For such an analysis, the object to be examined requires an image of the object from a 360° periphery, which requires the use of multiple cameras when using the conventional methods.

An additional disadvantage to the use of the known methods lies in the fact that the visual lines of the camera diverge during optical imaging by means of a camera, particularly when short focal distances are used. This is due to the fact that the optical image of a camera is fundamentally a central projection. This is a disadvantage when, for example, an adhesive or sealing bead is viewed from the top and said view is used to draw conclusions regarding properties of the object from the side because, depending on the angle of view, it is typical for one edge to be poorly visible or not visible at all.

SUMMARY OF THE INVENTION

The object of the present invention is therefore to create an optical monitoring device that allows an analysis of a three-dimensional object in the monitoring range by means of a camera, particularly from all sides, although the camera is to be essentially disposed above the monitoring area.

The object stated above is attained by a monitoring device that provides at least one first mirror that is bent concavely in at least a partial region, said mirror being disposed in the optical path between the monitoring area and the camera.

The advantage of such an optical monitoring device according to the invention lies in the fact that, due to the concavely bent first mirror, the visual lines of the camera are deflected such that examination of the three-dimensional object is made possible from a desired side, even though the camera is disposed above the monitoring area. In particular, the first mirror may be disposed such that a good view of the edges is obtained.

Moreover, the field of view is deformed in an advantageous fashion by the bent mirror such that the camera is able to cover a large portion of the monitoring area.

In a preferred exemplary embodiment, the first mirror is embodied as an annular mirror whose inner contour preferably has an essentially circular or elliptical design. Such a mirror deflects the visual lines of the camera so as to allow a 360° view of the object disposed in the monitoring area. The term "inner contour of the mirror" is understood in this context to mean the line forming the contour of the mirror located farthest inwards when the mirror is viewed from the direction of the longitudinal axis. The recess in the annular mirror limited by the inner contour preferably serves to accommodate the tool.

In an additional preferred exemplary embodiment, the camera and the first mirror are disposed such that the visual range of the mirror captures the monitoring area from the side, i.e., the visual lines of the camera contact the monitoring area from the side. Here, the monitoring area is captured from at least one side, preferably from both sides at the same time, due to the fanning out of the visual lines by the concavely bent first mirror.

The first mirror is preferably bent such that a cross section of the mirror forms an elliptical or circular section, at least in sections. In an additional preferred exemplary embodiment, the midpoint of the cross section (if said cross section forms a circular section or elliptical section at least in sections) of the annular mirror is not disposed on the longitudinal axis of the tool.

Furthermore, it is preferred for the camera and the first mirror to be disposed such that the visual range of the camera runs at least partially radially relative to the longitudinal axis of the tool. This simplifies the analysis of the images generated by the camera.

In an additional exemplary embodiment, at least one component of the axis of the line of sight of the camera has a radial course relative to the first mirror upon impacting the same. Moreover, the line of sight is directed outwards. Such a course of the line of sight of the camera allows the three-dimensional object to be captured from the side in any position.

In order to obtain a more favorable design, at least one second mirror, preferably having a flat design, may be provided and be disposed in the optical path between the camera and the first mirror and/or between the first mirror and the monitoring area. Such a flat mirror may deflect the beam path of the camera as often as desired.

In another exemplary embodiment, the first mirror and/or the second mirror have a pivotable and/or displaceable design. This allows the monitoring device to be adapted in a simple fashion to the current conditions of the monitoring area.

Preferably, at least two cameras, preferably three or four cameras, are provided in the monitoring device, which are preferably disposed such that the fields of view of the cameras overlap. This allows the monitoring area to be covered in a duplicate fashion and attains a redundancy for the monitoring process.

Moreover, it is advantageous for the first mirror and the camera to be attachable to the tool such that the field of view of the camera is always oriented towards the monitoring area. This guarantees that the monitoring device always captures the monitoring area, thus eliminating tracking of the monitoring device and the equipment expense and technical effort associated therewith.

In order to achieve a high quality of monitoring, it can be advantageous for constant light conditions to prevail during monitoring. Therefore, it is advisable for an illumination device to be provided on the monitoring device; the illumination device may be composed of one or more light fittings or segments. Thus, the illumination device also tracks the movement of the tool and the visibility conditions in the monitoring area are kept constant. The illumination device may be specially adapted to certain monitoring tasks. To this end, the illumination device in one exemplary embodiment of the monitoring device according to the invention may be embodied as a flash unit or as a continuous lighting unit.

According to the invention, the optical monitoring device further comprises an analysis device, particularly a computer system, which serves to control the camera, the first mirror, the second mirror, the illumination device, the light line device, and/or for analyzing the images from the camera. Such an analysis device is connected to the optical monitoring device, receives camera data and/or signals, and analyzes them correspondingly. The analysis device is preferably configured to perform three-dimensional measurements (for example, using triangulation) and serves, for example, to inspect and/or measure the work performed by the tool in the monitoring area. This may in particular be achieved using image recognition software adapted to a specialized application. This software may analyze images, recognize geometric structures, evaluate differences in brightness, perform a comparison to reference images, determine dimensions, and/or perform other appropriate analyses of the camera images.

The preferred option for performing three-dimensional measurements is to project an annular light line vertically from above onto the monitoring area. However, the light line may have a different shape as well (for example, a plurality of bent lines, a plurality of straight lines); but the annular shape is advantageous in the case of an application involving a field of view around an applicator. If the light line and the camera are calibrated to one another, a triangulation measurement that is known per se may be performed at each point where one of the cameras of the monitoring device see the light line or strip of light hitting the object to be measured, and the three-dimensional dimensions of the three-dimensional object disposed in the monitoring area may thus be determined. Various known methods may be used for the calibration, for example, the recording of a calibration characteristic curve.

Another option for three-dimensional measurement is to form stereo pairs from the images of two respective cameras and to analyze said stereo pairs while taking into account the arrangement of the cameras and the arrangement of the first mirror and, optionally, the second mirror. Moreover, it is particularly advantageous for the image capture by all cameras of the monitoring device to occur in parallel and for a real-time processing of the images thus obtained to be performed, such that the cameras may be used for measurement during ongoing operation.

The monitoring device according to the invention may be used for tools that move as well as for stationary tools past which an object to be processed moves.

Further developments, advantages, and application options of the invention may be found in the following description of an exemplary embodiment of the present invention and in the drawing. All of the features of the invention described and/or shown therein, alone or in combination, shall be considered components of the invention regardless of their combination in the Claims or the dependency of said Claims.

BRIEF DESCRIPTION OF THE DRAWINGS

The drawing shows schematically:
FIG. 1 a monitoring device according to the invention in a top view.

DETAILED DESCRIPTION OF THE INVENTION

For the sake of simplicity, only one camera of the monitoring device is shown in the figure.

The optical monitoring device according to the invention comprises two cameras 1 having a lens and an annular mirror 2 disposed above the cameras 1. Additionally, an applicator 3 that applies an adhesive bead 5 to a substrate is provided as an example of a tool to be monitored. The feed direction of the applicator 3 is shown in FIG. 1 with the reference number 6. The applicator 3 is disposed in the section limited by the circular inner contour (see line with reference number 2 in FIG. 1) of the annular mirror.

In order to protect the cameras 1 with the lenses, the monitoring device may comprise a housing that accommodates the cameras 1.

In the exemplary embodiment shown, an area has been selected as the monitoring area 20 that extends around the working area of the applicator 3. The monitoring area 20 extends in an area approximately the shape of a hollow cylinder (circular cylinder) around the longitudinal axis of the applicator 3. Here, the longitudinal axis of the applicator 3 runs perpendicular to the view in FIG. 1. The outer limits of the monitoring area 20 are depicted in FIG. 1 by dashed lines. However, the monitoring area may also be configured at any other location desired, preferably at locations associated with the work of the applicator 3.

The optical path extends from the monitoring area 20 over the annular mirror 2 to the respective camera 1. Optionally, a flat mirror may be disposed in the optical path between the monitoring area 20 and the annular mirror 2 or between the annular mirror 2 and the camera 1.

In addition, a light line device (not shown) is provided that generates a circular light line 9 on a flat underlay running perpendicular to the axis of the light line. The light line is shown in FIG. 1 as a bold line 9 and extends past the adhesive bead 5. At each point where the light line 9 extends past the adhesive bead, a triangulation may be performed and the data thus obtained may be used to determine the three-dimensional dimensions of the adhesive bead 5, for example, its height. The line may, for example, be generated with the aid of a laser and a corresponding annular lens.

The monitoring device additionally comprises an illumination device that projects a light circle 7 onto the monitoring area 20 in the direction of the longitudinal axis of the applicator 3. In the exemplary embodiment shown, the light line 9 is disposed such that it extends in the edge region of the light circle 7.

The three cameras 1 are disposed around the applicator 3 essentially on a circular path such that the visual lines 4 of each camera 1 are each directed towards a partial region of the monitoring area 20 after reflection on the annular mirror 2. Here, the axis (shown as a central visual line 4') of the line of sight of each camera 1 runs radially relative to the annular mirror 2. The line of sight of each camera 1 is moreover directed outwards from the inner region of the annular mirror 2. FIG. 1 shows that the outer visual lines first diverge as they originate from the camera 1 and, after reflection on the annular mirror 2, are merged again due to its annular shape. The central visual line 4' runs approximately radially to the longitudinal axis of the applicator 3. By this arrangement of the cameras 1 and the annular mirror 2 and the bend of the annular mirror 2, the use of only a small number of cameras is required because each camera 1 covers a larger portion of the monitoring area.

The outer visual lines 4 of the cameras 1 also capture the region of the monitoring area 20 located farthest below and hit the monitoring area from the side (laterally). Thus, it is possible for the dimensions of the adhesive bead 5 to be captured in all dimensions, particularly in the dimension running in the direction of the vertical axis. This allows the entire monitoring area 20 to be monitored from the side at the same time.

FIG. 1 does not show the illumination device generating the light circle 7 or the analysis device embodied as a computer system. The images generated by the cameras 1 are transmitted to the analysis device such that they may be processed, for example, with regard to the dimensions of the adhesive bead 5, particularly with regard to the height of the adhesive bead 5. Preferably, image recognition software is used for this purpose and a triangulation method is used.

By means of the monitoring device according to the invention shown in the drawings, it is possible to examine a monitoring area from all sides at the same time.

LIST OF REFERENCE CHARACTERS

1 Camera with lens
2 Annular mirror
3 Applicator
4, 4' Visual line
5 Adhesive bead
6 Feed direction
7 Light circle
9 Light line
20 Monitoring area

What is claimed is:

1. An optical monitoring device for monitoring the activity of a tool (3) in a monitoring area (20), comprising:
at least one camera (1), and
a first annular mirror (2) that is concavely bent in at least one partial region and disposed in an optical path between the monitoring area (20) and the camera (1);
wherein during operation, the tool (3) is positioned within a recess of the first annular mirror, which recess is limited by an inner contour of the mirror,
wherein the camera (1) and the first annular mirror (2) are disposed such that a field of view of the camera (1) runs at least partially radially relative to a longitudinal axis of the tool (3),
wherein the field of view of the camera (1) captures the monitoring area (20) from outside the monitoring area (20) directed into the monitoring area (20),
wherein the first annular mirror (2) and the camera (1) are attachable to the tool (3) such that the field of view of the camera (1) is always oriented towards the monitoring area (20), and
wherein at least one component of the axis of the line of sight of the camera has a radial course relative to the first annular mirror upon impacting the first annular mirror.

2. The optical monitoring device according to claim 1, wherein the inner contour of the first annular mirror (2) has an essentially circular or elliptical design.

3. The optical monitoring device according to claim 1, wherein the midpoint of the cross section of the first annular mirror (2) is disposed next to the longitudinal axis of the tool (3).

4. The optical monitoring device according to claim 1, wherein the cross section through the first annular mirror (2) has the shape of a circular or elliptical section.

5. The optical monitoring device according to claim 1, wherein at least one component of the axis of the line of sight of the camera (1) runs radially relative to the first annular mirror (2) after hitting said mirror and in that the line of sight is directed outwards.

6. The optical monitoring device according to claim 1, further comprising at least one second mirror having a flat design disposed in the optical path between the camera (1) and the first annular mirror (2) and/or between the first annular mirror (2) and the monitoring area (20).

7. The optical monitoring device according to claim 6, wherein the first annular mirror (2) and/or the second mirror is designed to be pivotable or displaceable.

8. The optical monitoring device according to claim 6, further comprising an analysis device that serves to control the camera (1), the first annular mirror (2), the second mirror, the illumination device, and/or to analyze the images from the camera (1).

9. The optical monitoring device according to claim 8, wherein the analysis device is configured for conducting three-dimensional measurements.

10. The optical monitoring device according to claim 1, further comprising at least two cameras (1) having overlapping fields of view.

11. The optical monitoring device according to claim 1, further comprising an illumination device embodied as a flash unit or as a continuous lighting unit.

12. The optical monitoring device according to claim 1, further comprising a light line device that generates a light line (9) in the monitoring area (20) for conducting a three-dimensional triangulation measurement.

13. The optical monitoring device according to claim 1, where a line of sight of the camera (1) is directed radially outwards.

14. The optical monitoring device according to claim 1, wherein the at least one camera (1) is positioned on an inner side of the first annular mirror (2).

* * * * *